United States Patent [19]

Lopez

[11] Patent Number: 4,600,003
[45] Date of Patent: Jul. 15, 1986

[54] INTRAOCULAR LENS INSERTING TOOL

[76] Inventor: Octavio Lopez, 111 N. Wabash Ave., Chicago, Ill. 60602

[21] Appl. No.: 415,804

[22] Filed: Sep. 8, 1982

[51] Int. Cl.4 .......................... A61B 17/00; A61F 2/16
[52] U.S. Cl. ..................................... 128/303 R; 623/6
[58] Field of Search .............. 3/13; 128/303 R; 623/6

[56] References Cited

U.S. PATENT DOCUMENTS

| 3,991,426 | 11/1976 | Flom et al. | 128/303 R X |
| 4,136,406 | 1/1979 | Norris | 3/13 |
| 4,190,049 | 2/1980 | Hager et al. | 128/303 R |
| 4,251,887 | 2/1981 | Anis | 3/13 |
| 4,349,027 | 9/1982 | DiFrancesco | 128/303 R |

Primary Examiner—Ronald L. Frinks
Attorney, Agent, or Firm—Kane, Dalsimer, Kane, Sullivan and Kurucz

[57] ABSTRACT

A tool for inserting an intraocular lens into an eye having an elongated flat member with a wide end, and two side walls for closing the haptics of lens around the lens. The lens is placed on the wide end and after the narrow end is inserted into the eye through an appropriate opening, the lens is slid along the tool into the eye.

5 Claims, 6 Drawing Figures

INTRAOCULAR LENS INSERTING TOOL

BACKGROUND OF THE INVENTION

This invention pertains to a tool for inserting an intraocular lens into the eye.

Various diseases of the human eye may require removal of the eye's natural lens. For example, one of these diseases causes the natural lens to become opaque, thus blocking the light before it hits the retina. This effect is commonly referred to as a cataract.

After the lens has been removed, an artificial lens must be provided to restore the patient's vision. Generally, there are three methods of providing such lens: regular glasses, external contact lens and intraocular lens.

Regular glasses used for cataracts are very thick and therefore found aesthetically objectionable by many patients. Contact lenses are inappropriate to some patients, especially older ones who do not have the dexterity necessary for inserting or removing the lens. Thus, for many patients the intraocular lenses present the best alternative.

Depending on their actual position within the eye, intraocular lenses are categorized either as anterior chamber lenses or posterior chamber lenses. As the name implies an anterior chamber lens is installed in the anterior chamber between the iris and the ocular jelly. Sometimes, this lens is positioned in the plane of the iris. In order to insure that the lens does not shift, the lens is sometimes sutured or otherwise affixed to the iris. Anterior chamber lenses are the predominant and safer type of lenses, and, of course, they must be used after intracapsular surgery, during which the capsular bag is removed.

Posterior chamber lenses can be used after extracapsular surgery, i.e., when the cataract is removed but the capsular bag is left in place. Although posterior chamber lenses may be positioned between the bag and the iris, it was found that it is safer to install these lenses within the capsular bag itself.

Intraocular lenses have gone through an evolution of their own. While the initial lenses had bulky, complicated appendages for securing the lens within the eye, the latest lenses have much simpler mechanisms. One of the most common types of intraocular lens has a number of flexible loops or haptics. In the relaxed position, these loops are coplanar with the lens and engage the side walls of the eye in a spring action, thus holding the lens in place. The loops are made of polypropylene or other similar material and lenses are available with loops of a variety of sizes, shapes and colors.

It is well known that eye surgery is a very delicate procedure. Any inadvertent move on the part of the surgeon may further damage the eye. This is especially true for the process of implanting an intraocular eye because the lens itself is very small and, further, it must be precisely positioned so that it can focus the light entering the eye onto the retina. The lenses with loops are especially difficult to install because the loops in their open position cover an area which is much larger than the actual area of the lens. Various devices have been made which assist the surgeon in this procedure, however most of them are too bulky and expensive.

One device which has been used in particular with lenses having loops is the so-called SHEET GLIDE. This device is simply a flat flexible plastic strip which is slightly narrower than the diameter of the lens. In order to use this device, the surgeon makes an appropriate incision in the eye, and then slips the SHEET GLIDE into the eye with its tip positioned in the general location to be occupied by the lens. Next, he slides the lens on the glide into the eye. The incision in the eye must be large enough to accommodate the loops, and the SHEET GLIDE does not provide any protection of the eye during the implantation.

OBJECTIVES AND SUMMARY OF THE INVENTION

Therefore, it is the objective of this invention to provide a tool for inserting an intraocular lens in the eye which protects the eye during insertion.

Another objective is to provide a tool which requires a smaller opening then previously disclosed, thus making the operation safer.

A further objective is to provide a tool which keeps the loops close to the lens while the lens is being positioned within the eye.

Other objectives and advantages of the invention shall be described in the following description.

In accordance with the invention there is provided a tool for inserting an intraocular lens with loops or haptics, comprising a flat elongated member with two long sides, two opposing ends, and side walls disposed along said opposing sides.

After an incision is made in the eye, one end of the member is inserted through the incision and extended to the desired location of the lens. The lens is then placed on the other end and made to slide along the member until it reaches the desired position. The two side walls engage the haptics, and force the loop in a closed position around the lens.

DESCRIPTION OF THE PREFERRED EMBODIMENT

A preferred embodiment of the invention shall now be described in relation to a posterior chamber lens. It must be understood however that the device would work equally well with an anterior chamber lens.

Referring to FIGS. 1-6, a typical intraocular lens 10 comprises a lenticular body 20 which is made out of a transparent material and has the required optical characteristics necessary to correct the patient's vision. A number of holes such as 30 are provided within the body to allow the surgeon to manipulate the lens. Imbeded in the body are two haptics or loops 40 and 50. These loops are flexible, have a curvilinear shape in their relaxed or open position, and may be wrapped around the circumferance of the body 20.

Figure 1:
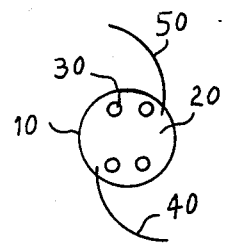
FIG. 1 shows a typical intraocular lens having haptics.
Figure 2:
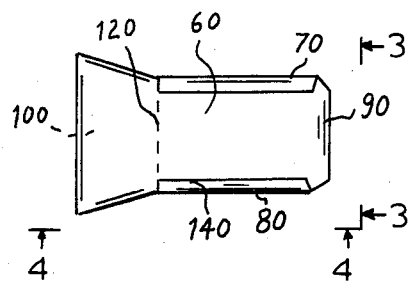
FIG. 2 is a plan view of the invention.
Figure 4:
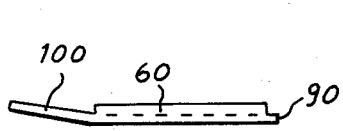
FIG. 4 is a side view of the invention.
Figure 3:
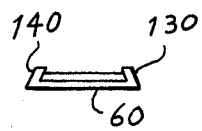
FIG. 3 is an end view of the invention.
Figure 5:
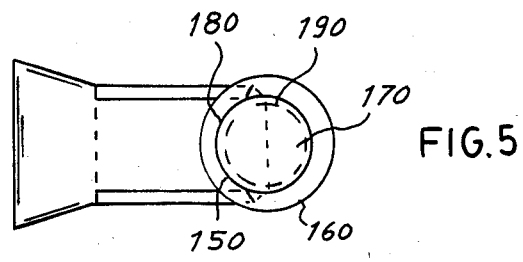
FIG. 5 shows the tool being inserted into the capsular bag of an eye.

The tool itself comprises a flat member 60 with sides 70 and 80, and ends 90 and 100. The member 60 is slightly wider than lens 10 to accomodate both the lens and the haptics. End 90 has an arcuate shape, and end 100 has a trapezoidal shape with a small base 120 which corresponds to the width of member 60 as shown in FIG. 2, except for base 120, the end 100 has a dimension transversal to a longitudinal axis of the flat member 60 which is wider than the flat member. As can be best seen in FIG. 4, end 100 is at slight angle with respect to member 60. Affixed to sides 70 and 80 respectively are two side walls 130 and 140. Preferably the two side walls may lean toward each other at a predetermined angle as shown in FIG. 3. The invention as it appears during the insertion process is shown in FIG. 5.

Figure 6:
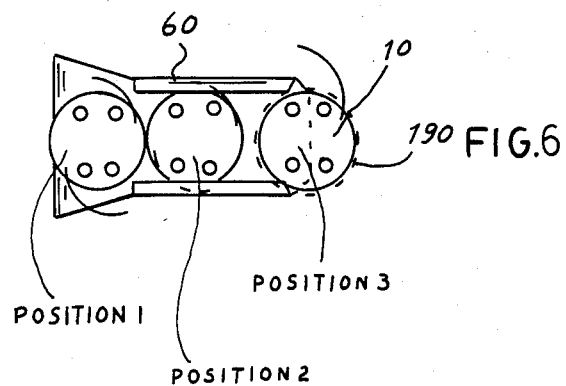
FIG. 6 shows the different positions of the lens as it slides along the tool.

Prior to the insertion of the lens, an incision 150 is made in eye 160 between the corner 170 and the choroid tissues 180. The incision 150 need not be wider than the width of member 60. End 90 is next extended into the capsular bag 190 until it reaches the desired position. Next, the lens is placed on trapezoidal end 100 and then slipped between side walls 130 and 140 (as shown in FIG. 6) so that the haptics are wrapped around the lens in a closed shape. (FIG. 6, Position 1). This phase is facilitated by the angle between the trapezoidal end 90 and member 60. Once the lens is pushed between the two walls, as in position 2, the walls insure that the loops don't jump out because said walls lean toward each other. Once the lens is in the desired position (position 3) it is slipped off from the tool, and the haptics open up to secure the lens within the capsular bag. Any standard surgical tool may be used to guide the lens 10 along member 60.

One skilled in the art will appreciate the fact that during insertion, the haptics are held closed, and therefore, the risk of injuring the eye is reduced. Member 60 also protects the capsular bag while the lens is being inserted. This facet of the invention becomes very important when the invention is used for an anterior chamber lens. As it was previously shown, the anterior chamber lens is installed above the iris, and above the ocular jelly contained in the anterior chamber During any surgical operation, contact with this jelly must be avoided as much as possible. If the present invention is used to insert the lens, the jelly is protected by member 60.

The tool may be made of any of the common plastics in use today. Since it is very inexpensive to manufacture, it may be disposed after a single use, thus saving the sanitizing costs. Its size depends on the size of the lens. Preferably the member 60 should be about 10–12 mm long by 6–8 mm wide. Trapezoidal end 100 can have a large base of 12–14 mm and a height of 8–10 mm. Walls 70 and 80 may have a height of 1–1.5 mm.

In summary, the present invention provides an inexpensive tool for inserting an intraocular lens in an eye by keeping the haptics closed until after the lens has been positioned, and without the use of awkward and bulky instruments. The tool also protects the eye during the insertion procedure.

It will be apparent to those skilled in the art that various modifications of the invention may be made without departing from the scope of the invention as defined in the appended claims.

I claim:

1. A tool for inserting an intraocular lens with haptics into an eye comprising:
    an elongated flat member having a longitudinal axis, a top surface and bottom surface;
    two opposed spaced side walls at least partially extending longitudinally along said member and terminating above said top surface and adapted to engage said haptics and force them into a closed position around said lens when a portion of said tool is inserted into the eye and said lens is disposed with the eye by sliding it on said flat member between said side walls;
    a first end connected to said flat member provided for holding said lens prior to insertion, said first end having a dimension transversal to said longitudinal axis of said flat member, said dimension being larger than a width of said member; and
    a second end connected to said flat member opposite said first end adapted to facilitate the insertion of the tool into the eye.

2. The tool of claim 1 wherein said two side walls lean toward each other.

3. The tool of claim 1 wherein said first end is at a predetermined angle to said member.

4. The tool of claim 1 wherein said first end is trapezoidal and has two bases oriented perpendicularly to said side walls.

5. A tool for inserting an intraocular lens with two haptics into an incision of an eye comprising:
    a flat member having a width of 6–8 mm, a length of 10–12 mm;
    two opposing side walls disposed along said length, and leaning toward each other and having a height of 1.5 mm; and
    a trapezoidal end with a short base equal to said width, a long base of 12–14 mm and a height of 8–10 mm; said end being attached to said flat member and adapted to hold a lens adjacent to said side walls and;
    an arcuate end attached to said flat member opposite said trapezoidal end;
    whereby said lens is inserted into said eye by disposing said arctuate end within said eye through the incision; placing the lens on said trapezoidal end and sliding it between said side walls toward said arcuate end.

* * * * *